United States Patent
Back

(10) Patent No.: US 11,401,228 B2
(45) Date of Patent: Aug. 2, 2022

(54) PROCESS FOR THE DIRECT ALPHA-METHYLENATION OF KETONES

(71) Applicant: RHODIA OPERATIONS, Aubervilliers (FR)

(72) Inventor: Olivier Back, Lyons (FR)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 17/293,981

(22) PCT Filed: Nov. 18, 2019

(86) PCT No.: PCT/EP2019/081693
§ 371 (c)(1),
(2) Date: May 14, 2021

(87) PCT Pub. No.: WO2020/104398
PCT Pub. Date: May 28, 2020

(65) Prior Publication Data
US 2022/0002221 A1 Jan. 6, 2022

(30) Foreign Application Priority Data
Nov. 20, 2018 (EP) .................... 18306532

(51) Int. Cl.
*C07C 45/75* (2006.01)
(52) U.S. Cl.
CPC .................... *C07C 45/75* (2013.01)
(58) Field of Classification Search
CPC .................................................. C07C 45/75
See application file for complete search history.

(56) References Cited

PUBLICATIONS

Alejandro Bugarin, Kyle D. Jones, Brian T. Connell—Efficient, direct .alpha.-methylenation of carbonyls mediated by diisopropylammonium trifluoroacetate—Chem. Commun., 2010,46, 1715-1717—DOI: 10.1039/b924577d.

Anniina Erkkilä, Petri M. Pihko—Mild Organocatalytic [alpha]-Methylenation of Aldehydes—J. Org. Chem. 2006, 71, 6, 2538-2541—DOI/ 10.1021/jo052529q.

J-L. Gras—A direct synthesis of α-methylene ketones—Tetrahedron Letters (1978) 19(24) :2111-2114—doi: 10.1016/S0040-4039(01)94763-X.

J.L.Roberts, P.S. Borromeo, and C.D. Poulter—Addition of eschenmoser's salt to ketone, ester, lactone enolates. a convenient synthesis of a-methylene carbonyls via mannich intermediates—Tetrahedron (1977) Letters, 18 (19) :1621-1623—doi :10.1016/S0040-4039(01)93231-9.

J-L. Gras—A facile entry to vinyl ketones—Tetrahedron Letters (1978) 19(32) :2955-2958—doi: 10.1016/S0040-4039(01)94910-X.

G.S. Mironov, M.I. Farberov, and I.M. Orlova—Synthesis of carbonyl monomers by Mannich reaction. IV. New method for synthesis of divinyl ketones—Zhumal obshchei khimii (1963) 33 (5) :1512-1517.

*Primary Examiner* — Sikarl A Witherspoon
(74) *Attorney, Agent, or Firm* — Osha Bergman Watanabe & Burton LLP

(57) ABSTRACT

The invention relates to a process for preparing an α-methylene ketone comprising the step of reacting a ketone with formaldehyde in the presence of a catalyst which is an organic compound comprising at least one acid function or the corresponding salt, ester or amide thereof and at least one amine function or the corresponding ammonium salt, or a zwitterion thereof.

17 Claims, No Drawings

PROCESS FOR THE DIRECT ALPHA-METHYLENATION OF KETONES

CROSS REFERENCE TO A RELATED APPLICATION

This application is a U.S. national phase entry under 35 U.S.C. § 371 of International Application No. PCT/EP2019/081693, filed on Nov. 18, 2019, which claims priority to European application No. 18306532.5 filed on Nov. 20, 2018. The entire contents of these applications are explicitly incorporated herein by this reference.

TECHNICAL FIELD OF THE INVENTION

The invention relates to a process for preparing an α-methylene ketone comprising the step of reacting a ketone with formaldehyde.

BACKGROUND

Molecules containing an α,β-unsaturated carbonyl functionality are commonly utilized as substrates for a range of chemical transformations, including nucleophilic conjugate addition, Michael addition, the Morita-Baylis-Hillmann reaction, Diels-Alder reaction, and several other organocatalytic reactions. The importance of the α-methylene moiety is also amplified by its presence in numerous biologically active natural products. α-Methylenation reaction using formaldehyde as the electrophilic partner has attracted attention because it is generally an atom economical method for conversion of simple carbonyl compounds to their corresponding α,β-unsaturated derivatives.

Several methods have been developed for the α-methylenation of carbonyl compounds. In an early method described by J. L. Roberts, et al. in Tetrahedron Letters No. 19, pp. 1621-1624, 1977, the methylenation of ketone compounds using formaldehyde relied on a two-step chemical transformation: first a Mannich condensation provides an amine intermediate which is isolated and then quaternized in a second step to afford a quaternary ammonium derivative which can readily undergo an elimination reaction under basic conditions to afford the desired α,β-unsaturated ketone product along with an amine as by-product.

The first "one-pot"-process to realize the methylenation of ketone was report by J. L. Gras in Tetrahedron Letters No. 24, pp. 2111-2114, 1978. The reaction of the ketone with s-trioxane was mediated by N-methylaniline and trifluoroacetic acid.

A. Bugarin et al. describe in Chem. Commun., 46, 1715-1717, 2010, the α-methylenation of acetophenone with paraformaldehyde in the presence of diisopropyl ammonium trifluoroacetate. While with this catalyst good yields can be obtained, the catalyst is required in equimolar amounts relative to the ketone.

Therefore, there is still a need for further improving the direct methylenation of ketones with formaldehyde. It is, for example, desirable to have such methylenation process available which requires less catalyst and which therefore is environmentally more friendly and less costly.

SUMMARY OF THE INVENTION

The present inventors have now found that the methylenation reaction between ketones and formaldehyde can be catalyzed by cheap, bio-based and readily available organic compounds comprising at least one acid function and at least one amine function. The present invention therefore relates to a process for preparing an α-methylene ketone comprising the step of reacting a ketone with formaldehyde in the presence of a catalyst which is an organic compound comprising at least one acid function (or the corresponding salt, ester or amide thereof) and at least one amine function (or the corresponding ammonium salt) or a zwitterion thereof.

An advantage of the process of the invention is that the catalyst is able to catalyze the reaction at a rather low catalytic loading of, for example, only 10 mol %, based on the amount of the ketone. Thus, stoichiometric amounts of the catalyst as in the prior art methods are no longer required.

DETAILED DESCRIPTION

The present invention relates to a process for preparing an α-methylene ketone comprising the step of reacting a ketone with formaldehyde in the presence of a catalyst which is an organic compound comprising at least one acid function (or the corresponding salt, ester or amide thereof) and at least one amine function (or the corresponding ammonium salt) or a zwitterion thereof. In this process, the catalyst catalyzes the reaction between the ketone and the formaldehyde.

The methylenation reaction is exemplified by the following general reaction scheme:

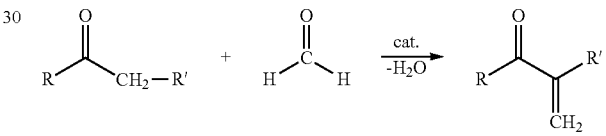

wherein R and R' can be defined as described below and "cat." is a catalyst.

The ketone can be any ketone which can react with formaldehyde to obtain a α-methylene ketone. Thus, the ketone must bear at least one methyl or methylene moiety next to the carbonyl moiety.

In one embodiment, the ketone used in the process of the invention has the general chemical formula (I)

wherein R is a hydrocarbon radical which may be interrupted by one or more heteroatoms and/or heteroatom(s) containing groups and/or which may be substituted with one or more functional groups, and
R' is H or a hydrocarbon radical which may be interrupted by one or more heteroatoms and/or heteroatom(s) containing groups and/or which may be substituted with one or more functional groups,
wherein R and R' together with the —C(O)—CH$_2$— moiety may form a ring.

In above formula (I), the residues R and R' are not particularly limited because the reaction between the ketone and the formaldehyde takes place at the —CH$_2$— moiety. Therefore, R and R' can be selected by the skilled person according to the desired end product.

For example, R and R' independently can comprise 1 to 30 carbon atoms, preferably 1 to 20 carbon atoms, such as 1 to 12 carbon atoms. In particular:

R and R' independently can be a hydrocarbon radical as such (meaning that it is uninterrupted and unsubstituted) comprising 1 to 30 carbon atoms, preferably 1 to 20 carbon atoms, such as 1 to 12 carbon atoms;

R and R' independently can also be a residue comprising 1 to 30 carbon atoms, preferably 1 to 20 carbon atoms, such as 1 to 12 carbon atoms, which residue consists in a hydrocarbon radical which is interrupted by one or more heteroatoms and/or heteroatom(s) containing groups and/or which is substituted with one or more functional groups;

The hydrocarbon radical may be interrupted by one or more heteroatoms and/or heteroatom(s) containing groups. The heteroatom can for example, be selected from N, O, S and P. As examples of heteroatom(s) containing groups, one can mention: carbonyl —C=O—, carboxy-(C=O)O—, carboxamide —(C=O)N, carbonate —O(C=O)O—, carbamate —O(C=O)N, urea N(C=O)N, sulfoxide —(S=O)—, sulfone —(SO$_2$)—, phosphate —(P=O)O$_3$—, and phosphonate —(P=O)O$_2$. In this context, "interrupted" means that the heteroatom and/or the heteroatom(s) containing group is situated between at least 2 carbon atoms.

Each hydrocarbon radical may be substituted with one or more functional groups which may, for example, be selected from halogen, hydroxyl, carbonyl, carboxyl, ester, amine, amide, imide, cyanate, isocyanate, nitro, sulfonyl, thiocyanate, isothiocyanate, and phosphate. Any functional group may be situated at any position of the hydrocarbon residue, and, in case of, for example, carbonyl or ester, may interrupt the hydrocarbon residue.

Suitable hydrocarbon radicals are, for example, alkyl, which may be linear or branched, alkenyl, which may be linear or branched, alkynyl, which may be linear or branched, cycloalkyl and aryl, in particular phenyl. Combinations of these groups are possible as well, such as, for example, combinations of linear and cyclic groups, such as alkylaryl, alkyl-cycloalkyl, arylalkyl and cycloalkyl-aryl groups. R and R' independently can be chosen from such suitable hydrocarbon radicals as such and from such suitable hydrocarbon radicals which are interrupted by one or more heteroatoms and/or heteroatom(s) containing groups and/or which are substituted with one or more functional groups.

Suitable residues for R are, for example, phenyl, halogen substituted phenyl, such as fluorophenyl, chlorophenyl, bromophenyl and iodophenyl, alkoxy phenyl, such as C$_{1-20}$ alkoxyphenyl, alkylphenyl, such as C$_{1-20}$ alkylphenyl, alkyl, such as C$_{1-20}$ alkyl, alkyl carboxylate of general formula R"—O—C(O)— wherein R" is a C$_{1-20}$ alkyl radical and an alkyl alkylenecarboxylate of general formula R"—O—C(O)—(CH$_2$)$_n$— wherein R" is a C$_{1-20}$ alkyl radical and n is an integer from 1 to 20.

R' can, for example, be H or any of the preferred embodiments described above for R wherein R and R' can be selected independently of each other. In certain embodiments, R' is H or C$_{1-20}$ alkyl.

In one embodiment, R and R' in above formula (I) together with the —C(O)—CH$_2$— moiety form a ring. Such ring can, for example, be a five-, six- or seven-membered ring. The ring may contain one or more heteroatoms, such as N, O, S, and P and/or heteroatom(s) containing groups as defined above.

Ketones comprising such ring are, for example, cyclopentanone, cyclohexanone, cycloheptanone, 3,3,5,5-tetramethyl cyclohexanone, 3,4-dihydro-2H-naphthalen-1-one and 2,3-dihydro-4-benzopyranone.

If R is selected such that the carbonyl moiety in the ketone is attached to a second —CH$_2$— moiety methylenation can occur at both —CH$_2$— moieties. In case of unsymmetrical ketones possessing two inequivalent methylene groups attached to the carbonyl moiety, good selectivity can be achieved with methylenation occurring at the less sterically crowed position.

In the process of the present invention, one single ketone or a mixture of two or more different ketones may be employed.

In one embodiment of the process of the invention, the reaction is conducted in the presence of an additional acid. This additional acid is present in addition to the catalyst and is different to this organic compound. It was found that such additional acid increases the catalytic activity of the catalyst. Suitable further acids may have a pK$_a$ value equal to or less than the pK$_a$ value of the acid function of the catalyst used in the reaction. In preferred embodiments, the further acid has a pK$_a$ value of less than 3, more preferably of less than 0.

The further acid may be an organic or an inorganic acid, inorganic acids being preferred. Examples for suitable inorganic acids are HCl, HBr, HI, H$_2$SO$_4$, HClO$_4$, HNO$_3$, and H$_3$PO$_4$. Examples of suitable organic acids are sulfonic acids, such as methanesulfonic acid and paratoluene sulfonic acid. The further acid may be a mono acid, such as HCl, or a multiple acid, such as H$_2$SO$_4$ or H$_3$PO$_4$. Additionally, the further acid may contain one or more acid functions. The further acid can be a single acid or a mixture of two or more different acids. Preferably, the further acid is HCl, which may be used as aqueous hydrochloric acid solution at a concentration of, for example, 37 wt %.

As catalyst in the process of the invention, any organic compound which has at least one acid function (or the corresponding salt, ester or amide thereof) and at least one amine function (or the corresponding ammonium salt) may be employed. As the organic compound has at least one acid function and at least one amine function within the same molecule, it may be present as a zwitterion. Such zwitterion is exemplified in the following reaction scheme showing an amino acid as one possible example for an organic compound used in the present invention:

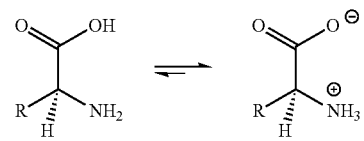

On the left side of this reaction scheme, the organic compound comprising a carboxyl radical (acid function) and an amine function is shown. The tautomer on the right is the corresponding zwitterion thereof.

It is intended that within the context of the present invention any organic compound having an acid function and an amine function includes the zwitterion thereof.

In such compound, the amino function can be any known amine group, in particular a primary or secondary amine. The acid function can be any known acid group, such as carboxylic acid, sulfonic acid or phosphonic acid. Carboxylic acid residues being preferred. For example, the catalyst can be a compound of the general formula (II)

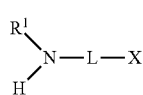
(II)

wherein $R^1$ is H or a hydrocarbon residue which may be interrupted by one or more heteroatoms and/or heteroatom(s) containing groups and/or which may be substituted with one or more functional groups,
X is an acid function or the corresponding salt, ester or amide, and
L is a linker, which has 1 to 6 atoms between N and X, wherein any atom of $R^1$ may be attached to any atom of L to form a ring,
or a zwitterion thereof.

The amine function in the catalyst can also be in the form of the conjugate ammonium salt, in this case the compound has the general formula (II'):

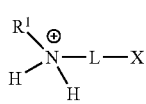
(II')

wherein $R^1$, L and X have the same definitions as above.

$R^1$ and preferred embodiments thereof are defined as R above. In a certain embodiment, $R^1$ is H or a $C_{1-6}$, preferably a $C_{1-3}$ alkyl radical, more preferably H, methyl, ethyl or propyl, more preferably H or ethyl, most preferably H.

The linker L may be a divalent hydrocarbon radical which may be interrupted by one or more heteroatoms and/or heteroatom(s) containing groups and/or which may be substituted with one or more functional groups as defined above for R including the preferred embodiments thereof, provided that L has 1 to 6 atoms between N and X, preferably 1 to 4 atoms, more preferably 1 to 3 atoms and most preferably 1 or 2, in particular 1 atom between N and X. The atoms between N and X preferably are carbon atoms but may also include heteroatoms, such as O, N, P and S. In addition to the atoms between N and X, the linker L may have further atoms, in particular carbon atoms and heteroatoms, such as O, N, P and S.

It is also possible that L forms or contains a ring which bridges N and X. In this case, the number of atoms between N and X is defined as the lowest number of atoms in any of the possible links between N and X. For example, if L is a 1,3-cyclohexan residue, one link between N and X has 3 atoms, while the other link has 5 atoms and, consequently, in the definition of compound (ii), L has 3 atoms between N and X.

If $R^1$ is not H, any atom of $R^1$ may be attached to any atom of L to form a ring including the nitrogen atom. For example, if L is a methine group and $R^1$ is a propylene group, $R^1$ may be attached to L to form a pyrrolidine ring, in which case the catalyst may be proline.

In the compound of formula (II) or (II') X is any acid function, such as carboxylic acid, sulfonic acid and phosphonic acid. Carboxylic acid residues being preferred.

In one embodiment, the catalyst has the general chemical formula (III)

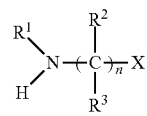
(III)

wherein $R^1$ and X are defined as above,
$R^2$ and $R^3$ in each occurrence and independently or each other, are H or a hydrocarbon radical which may be interrupted by one or more heteroatoms and/or heteroatom(s) containing groups and/or which may be substituted with one or more functional groups, and
n is an integer of 1 to 6, preferably 1 to 4, more preferably 1 or 2, most preferably 1,
wherein $R^1$ together with any of $R^2$ or $R^3$ may form a ring, or a zwitterion thereof.

As for the compound of formula (II) above, the amine function in the catalyst of formula (III) can also be in the form of the ammonium salt. In this case, the compound has the general formula (III'):

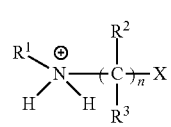
(III')

wherein $R^1$, $R^2$, $R^3$, n and X have the same definitions as above.

In one embodiment, $R^2$ is H or a linear or branched $C_{1-12}$, preferably a $C_{1-6}$ alkyl radical which may be interrupted by one or more, preferably one heteroatom, such as O, S, N and P, and which may be substituted by one or more aryl groups (in particular phenyl) and/or one or more heterocyclic groups, such as pyrazole or indol. The alkyl group, aryl group and heterocyclic group may be substituted with one or more functional groups, as defined above, in particular hydroxy.

$R^3$ preferably is H.

If n is above 1, it is preferred that only one of the carbon atoms bears a substituent $R^2$ other than H.

The catalyst may comprise one or more amino functions and one or more acid functions.

If applicable, the organic compound catalyst may be employed as a single enantiomer or as a racemic mixture.

Suitable salts of the catalyst are, for example, alkali metal or alkaline earth metal salts, in particular alkali metal salts, such as sodium and potassium salt. In the case the catalyst has its amine function protonated and is cationic, suitable salts of the catalyst are for example chloride, bromide, iodide, sulfate, hydrogen sulfate, phosphate etc.

The catalyst may be an amino acid, such as a natural amino acid.

Examples of suitable catalysts are glycine, valine, serine, methionine, cysteine, proline, sarcosine, β-alanine, phenylalanine, aminomethylphosphonic acid, taurine, methylalanine, isoleucine, and tert-leucine. Preferred amino acids are valine, proline, β-alanine, glycine and methylalanine, more preferably valine, β-alanine, glycine and methylalanine.

The reaction in the process of the invention may be conducted in the presence of a solvent. Such solvent is not particularly limited but should not interfere with the methylenation reaction. Suitable solvents are in particular organic solvents, such as DMSO, THF, methyl-THF, ethylacetate, toluene, benzene, acetone, dimethyl formamide, acetonitrile, alcohols, such as methanol, ethanol and isopropanol, halogenated, in particular chlorinated solvents, such as dichloromethane and chloroform, and ketones with the exception of ketones bearing a —CH$_2$— moiety next to the carbonyl group. Preferably, the reaction is conducted in DMSO as solvent.

The concentrations of the reactants, i.e. the ketone and the formaldehyde, the catalyst, and, if present, the further acid in the reaction mixture are not particularly limited and can be selected by a person skilled in the art according to the requirements. For example, the catalyst can be present at an amount of at least 1 mol %, preferably of at least 3 mol % and most preferably of at least 5 mol %, each based on the amount of the ketone. In this regard, it is noted that the reaction can be conducted batchwise or continuously. If the reaction is conducted batchwise, the present amounts and also the amounts and concentrations given below relate to the beginning of the reaction.

The upper limit of the amount of catalyst is not limited but a particular advantage of the process of the invention is that it is not required to use the catalyst in stoichiometric amounts as required for the prior art catalysts. A low catalyst load of, for example, less than 90 mol %, preferably of less than 60 mol %, more preferably of less than 45 mol % and most preferably of less than 25 mol %, based on the amount of the ketone, is therefore preferred.

Suitable amounts of catalyst are, for example, in the range of 1 mol % to less than 90 mol %, preferably 1 mol % to less than 60 mol %, more preferably 1 mol % to less than 45 mol %, and most preferably in the range of 1 mol % to less than 25 mol %, based on the amount of the ketone. Other suitable ranges can be selected by combining the above lower and upper limits of the amounts of the catalyst.

Also the concentration of the ketone in the reaction mixture can be selected by a person skilled in the art according to the requirements. Suitable concentrations are, for example, less than 5 mol/l, preferably less than 2 mol/l, and more preferably less than 1 mol/l, such as, for example, about 0.4 mol/l.

The molar ratio of the catalyst to further acid is also not particularly limited and can be selected by a person skilled in the art according to the requirements. For example the molar ratio of catalyst to further acid can be in the range of 0.1 to 3.0, preferably in the range of 0.1 to 2.5, more preferably in the range of 0.5 to 2.0 and even more preferably in the range of 0.5 to 1.5, such as about 1.

The formaldehyde can be employed in the process of the present invention in the form of gaseous formaldehyde, an aqueous formaldehyde solution, trioxane or, for example, as paraformaldehyde. The amount of the formaldehyde present is not particularly limited and can be, for example, at least 150 mol %, preferably at least 200 mol %, based on the amount of the ketone.

Depending on the solvent, if present, and the pressure, the reaction in the process of the present invention can be conducted at any suitable temperature. The temperature can be, for example, in the range of 25° C. to 200° C., preferably in the range of 70° C. to 130° C., and more preferably in the range of 80° C. to 120° C.

The time during which the reaction in the process of the invention is conducted is not particularly limited and can be selected according to the requirements. A higher reaction temperature usually allows for a shorter reaction time. Suitable reaction times are, for example, at least 15 minutes, preferably at least 30 minutes and more preferably at least 60 minutes. However, longer reaction time of 3 hours or 5 hours and above, such as 6 hours, are suitable as well.

Should the disclosure of any patents, patent applications and publications which are incorporated herein by reference conflict with the description of the present application to the extent that it may render a term unclear, the present description shall take precedence.

The following examples are given by way of non-limiting illustration of the present invention.

EXAMPLES

Example 1

This example shows a comparison of the catalytic performances for different amino acid catalysts for the methylenation of acetophenone (30 mol % amino acid, 30 mol % HCl$_{aq.}$, CH$_2$O 4.2 eq., DMSO, 80° C., 5 hours)

The reactions were conducted in a 25 mL round bottom flask equipped with a condenser and a magnetic stirrer. Amino acid (1.2 mmol) to test as a catalyst and paraformaldehyde (0.505 g, 16.8 mmol) were dissolved in DMSO (10 mL) and the mixture was stirred at room temperature. Aqueous hydrochloric acid solution (37 wt %) (99 µL, 1.2 mmol) was then added to the mixture followed by acetophenone (0.481 g, 4 mmol). The reaction was then heated at 80° C. under stirring for 5 h. Progress of the reaction was monitored thanks to gas chromatography by withdrawing 500 µL samples from the reaction mixture and using 1,2-dichlorobenzene as internal standard (internal calibration done for reactant and the product).

Table 1 shows the substrate conversion (TR), the yield (η), the selectivity toward the desired product (S) and the maximal selectivity measured during the course of the reaction ($S_{max}$):

TABLE 1

| Amino acid | TR (%, 5 h) | η (%, 5 h) | S (%, 5 h) | $S_{max}$ (%) |
|---|---|---|---|---|
| Glycine | 100 | 66 | 66 | 77 |
| Valine | 98 | 76 | 78 | 81 |
| Serine | 97 | 65 | 67 | 75 |
| Methionine | 90 | 63 | 71 | 73 |
| Cysteine | 99 | 63 | 64 | 69 |
| Proline | 72 | 59 | 82 | 82 |
| Sarcosine | 84 | 66 | 78 | 79 |
| β-Alanine | 89 | 74 | 83 | 83 |
| Phenylalanine | 94 | 68 | 72 | 76 |
| Aminomethyl phosphonic acid | 100 | 61 | 61 | 73 |
| Taurine | 74 | 56 | 77 | 92 |
| Methylalanine | 92 | 73 | 80 | 80 |
| Isoleucine | 96 | 64 | 66 | 67 |
| tert-Leucine | 88 | 62 | 71 | 74 |
| No amino acid | 12 | 1 | — | — |

The comparative experiment (last entry) in Table 1 shows that in the absence of the amino acid, no product is formed.

Example 2

This example shows a comparison of the catalytic performances for the best candidates selected in Example 1 at higher temperature (30 mol % amino acid, 30 mol % $HCl_{aq}$, $CH_2O$ 4.2 eq., DMSO, 100° C., 5 hours)

The reactions were conducted in a 50 mL round bottom flask equipped with a condenser and a magnetic stirrer. Amino acid (2.4 mmol) to test as a catalyst and paraformaldehyde (1.01 g, 33.6 mmol) were dissolved in DMSO (20 mL) and the mixture was stirred at room temperature. Aqueous hydrochloric acid solution (37 wt %) (198 μL, 2.4 mmol) was then added followed by acetophenone (0.962 g, 8 mmol). The reaction mixture was then heated at 100° C. under stirring until optimum yield was reached (it was observed that product yield reached a maximum value during the reaction).

Progress of the reaction is monitored by gas chromatography by withdrawing 500 μL samples from the reaction mixture and using 1,2-dichlorobenzene as internal standard (internal calibration done for reactant and the product).

Table 2 gives the best yield ($\eta_{max}$) obtained for the selected amino acids, the selectivity of the reaction (S) and the time needed to reach optimal yield ($t_{optimum}$).

TABLE 2

| Amino acid | $\eta_{max}$ (%) | S (%) | $t_{optimum}$ |
|---|---|---|---|
| Methylalanine | 74 | 80 | 1 h 30 |
| β-Alanine | 80 | 82 | 1 h 30 |
| Proline | 68 | 79 | 2 h 30 |
| Valine | 75 | 81 | 1 h |
| Tert-Leucine | 65 | 66 | 2 h 30 |

Example 3

The reactions were conducted in a 50 mL round bottom flask equipped with a condenser and a magnetic stirrer.

β-Alanine (at a given concentration) and paraformaldehyde (at a given stoichiometry with respect to the substrate) were dissolved in DMSO (20 mL) and the mixture was then stirred at room temperature. Aqueous hydrochloric acid 37 wt % (at a given stoichiometry with respect to the amino acid) was added to the mixture followed by acetophenone (at a given concentration).

The reaction was then stirred at 100° C. until optimum yield was reached. The quantities of β-alanine, paraformaldehyde, hydrochloric acid and acetophenone were modified during the study in order to optimize the reaction conditions while minimizing the catalyst loading.

Progress of the reaction was monitored by gas chromatography by withdrawing 500 μL samples from the reaction mixture and using 1,2-dichlorobenzene as internal standard (internal calibration done for reactant and the product).

In Table 3 the "mol %" of β-alanine and HCl are given relative to the amount of acetophenone. The amount of formaldehyde "eq." is given as molar equivalent relative to the amount of acetophenone. It can be seen from the data in Table 3 that the optimal ratio between the amino acid (β-alanine) and HCl is 1:1 (compare entries 4-7). The catalyst loading can be decreased down to 10 mol % (with respect to the substrate) while keeping similar yield toward the desired product (compare entries 8-11). Increasing the temperature to 110° C. degrades slightly the yield. Optimal temperature is at 100° C. (see entry 12). Increasing acetophenone concentration from 0.4 mol/L to 1 mol/L has also a negative impact on the yield of methylenated ketone product (entry 13). Performing the addition of formaldehyde in a sequential manner (2*2.1 equivalents) does not improve significantly the yield (entry 14). However, it is possible to use only 2.1 equivalents of $CH_2O$ instead of 4.2 while keeping the same performances (entry 15). Decreasing the catalyst loading to 5 mol % (and heating the reaction media at 110° C. in order to maintain acceptable kinetics) degrades the yield (entry 16).

The system was also compared under the optimal conditions (entry 15) with the best catalytic system described so far in the literature (A. Bugarin et al., Chem. Commun., 2010, 46, 1715-1717) using diisopropylamine:trifluoroacetic acid as the catalytic system (entry 18). The prior art catalyst provided only trace amounts of product when used at 10 mol % after 6 h00 stirring at 100° C.

TABLE 3

| Entry | T (° C.) | [β-alanine] (mol %) | [HCl] (mol %) | [acetophenone] (mol · L$^{-1}$) | $CH_2O$ (eq.) | $\eta_{max}$ (%) | S (%) | $t_{optimum}$ |
|---|---|---|---|---|---|---|---|---|
| 1 | 80 | 30 | 30 | 0.4 | 4.2 | 74 | 83 | ≥5 h |
| 2 | 100 | 30 | 30 | 0.4 | 4.2 | 80 | 82 | 1 h 30 |
| 3 | 100 | 0 | 30 | 0.4 | 4.2 | 1 | — | — |
| 4 | 100 | 30 | 30 | 0.4 | 4.2 | 80 | 82 | 1 h 30 |
| 5 | 100 | 30 | 15 | 0.4 | 4.2 | 20 | 48 | 1 h |
| 6 | 100 | 30 | 36 | 0.4 | 4.2 | 71 | 73 | 1 h |
| 7 | 100 | 30 | 45 | 0.4 | 4.2 | 71 | 74 | 0 h 30 |
| 8 | 100 | 30 | 30 | 0.4 | 4.2 | 80 | 82 | 1 h 30 |
| 9 | 100 | 40 | 40 | 0.4 | 4.2 | 72 | 72 | 1 h |
| 10 | 100 | 20 | 20 | 0.4 | 4.2 | 77 | 79 | 2 h 30 |
| 11 | 100 | 10 | 10 | 0.4 | 4.2 | 77 | 83 | 5 h |
| 12 | 110 | 10 | 10 | 0.4 | 4.2 | 75 | 78 | 3 h |
| 13 | 100 | 10 | 10 | 1 | 4.2 | 67 | 72 | 3 h 30 |
| 14 | 100 | 10 | 10 | 0.4 | 2 × 2.1[a] | 75 | 78 | 5 h |
| 15 | 100 | 10 | 10 | 0.4 | 2.1 | 77 | 82 | 6 h |
| 16 | 110 | 5 | 5 | 0.4 | 2.1 | 64 | 74 | 6 h |
| 17 | 100[b] | 10 | 10 | 0.4 | 2.1 | 35 | 65 | 6 h |
| 18 | 100 | 10[c] | 11[c] | 0.4 | 2.1 | 4 | 23 | 6 h |

[a]After 3 h, the reaction was cooled down at room temperature for 30 minutes. A second addition of paraformaldehyde (2.1 equivalents) was done and the reaction mixture was stirred again at 100° C.
[b]Results obtained from a recycled catalyst. After a reaction conducted under the optimal conditions (entry 15), the product was extracted using diisopropyl ether. A new loading of substrate and paraformaldehyde was done and the reaction was started again under the same conditions.
[c]Comparative test with the best catalytic system found in the literature: diisopropylamine - trifluoroacetic acid 1:1.1 used at 10 mol %.

Example 4

The reactions were conducted in a 250 mL round bottom flask equipped with a condenser and a magnetic stirrer. β-alanine (0.446 g, 5 mmol) and paraformaldehyde (3.153 g, 105 mmol) were dissolved in DMSO (125 mL) and the mixture was stirred at room temperature. Aqueous hydrochloric acid 37 wt % (411 µL, 5 mmol) was added followed by the reactant that is evaluated (50 mmol). The reaction is then allowed to stir at 100° C. until optimum yield was observed.

Reaction monitoring: a sample (500 µL) was withdrawn from the reaction mixture and analyzed by GC using 1,2-dichlorobenzene as the internal standard (qualitative assessment only as internal calibration has not been performed for all the studied substrates).

OR a sample (500 µL) was withdrawn from the reaction mixture and was mixed with 1,2,4,5-tetramethylbenzene (15 mg) used as internal standard for NMR analysis. The $^1$H NMR was performed in $CDCl_3$ (750 µL) in order to follow up the reaction in terms of transformation rate and yield.

Once the optimal yield was reached, the reaction mixture was allowed to cool down at room temperature and the product was then extracted using diisopropyl ether (6×125 mL) or dichloromethane in the case of tricosanone. An additional extraction with diisopropyl ether (190 mL), after addition of a saturated $NaCl_{aq.}$ solution (60 mL), was sometimes required if the compound was hardly extracted by the direct extraction. All the organic phases were collected and the solvent removed under vacuum to recover the crude oil, which was then quantitatively analyzed by $^1$H NMR (with 1,2,4,5-tetramethylbenzene as internal standard) in order to assess the isolated yield.

The results are reported in the table 4:

TABLE 4

| Entry: | Substrate: | Product: | $T_{reaction}$ | Yield (%) |
|---|---|---|---|---|
| 1 | acetophenone | phenyl vinyl ketone | 6 h | 74% |
| 2 | 4'-fluoroacetophenone | 1-(4-fluorophenyl)prop-2-en-1-one | 5 h | 79% |
| 3 | 4'-chloroacetophenone | 1-(4-chlorophenyl)prop-2-en-1-one | 5 h 20 | 71% |
| 4 | 4'-bromoacetophenone | 1-(4-bromophenyl)prop-2-en-1-one | 4 h 45 | 65% |
| 5 | 4'-methoxyacetophenone | 1-(4-methoxyphenyl)prop-2-en-1-one | 5 h 50 | 78% |
| 6 | 4'-methylacetophenone | 1-(4-methylphenyl)prop-2-en-1-one | 6 h 15 | 75% |
| 7 | 2'-methylacetophenone | 1-(2-methylphenyl)prop-2-en-1-one | 6 h | 80% |

TABLE 4-continued

| Entry: | Substrate: | Product: | $T_{reaction}$ | Yield (%) |
|---|---|---|---|---|
| 8* | PhC(O)CH2C10H21 | PhC(O)C(=CH2)C10H21 | 24 h* | 48%* |
| 9* | tBu-C(O)-CH3 | tBu-C(O)-C(=CH2)H | 6 h 30* | 78%* |
| 10* | iPr-CH2-C(O)-CH3 | (three products) | 3 h 00* | 52%* |
| | | 42:1:4 | | |
| 11* | C5H11-CH2-C(O)-CH3 | (three products) | 5 h 30* | 54%* |
| | | 1:2:4 | | |
| 12* | C10H21-CH2-C(O)-CH2-C10H21 | C10H21-C(=CH2)-C(O)-CH2-C10H21 | 24 h* | 48%* |
| 13 | cyclohexanone | 2-methylenecyclohexanone | 2 h 00 | — |
| 14 | methyl pyruvate | methyl 2-oxo-3-butenoate | 2 h 00 | 7% |
| 15 | methyl acetoacetate | methyl 2-methylene-3-oxobutanoate | 2 h 00 | 14% |
| 16* | methyl levulinate | (four products) | 5 h 00* | 42%* |
| | | 1.4:1:1:1 | | |

*Reactions have been conducted using 20 mol % β-alanine-HCl aq

NMR Data for the Methylenated Ketone Products:

1-phenylprop-2-en-1-one

RMN $^1$H (CDCl$_3$, 400 MHz): δ 7.80 (m, 2H), 7.45 (m, 1H), 7.35 (m, 2H), 7.03 (dd, 1H, J=10.5 17.1 Hz), 6.29 (dd, 1H, J=1.7 17.1 Hz), 5.81 (dd, 1H, J=1.7 10.5 Hz).

1-(4-fluorophenyl)prop-2-en-1-one

RMN $^1$H (CDCl$_3$, 400 MHz): δ 7.89-7.85 (m, 2H), 7.07-7.0 (m, 3H), 6.32 (dd, 1H, J=1.7 17.1 Hz), 5.83 (dd, 1H, J=1.6 10.6 Hz).

1-(4-chlorophenyl)prop-2-en-1-one

RMN $^1$H (CDCl$_3$, 400 MHz): δ 7.76 (d, 2H), 7.33 (d, 2H), 7.00 (dd, 1H, J=10.6 17.1 Hz), 6.3 (dd, 1H, J=1.6 17.1 Hz), 5.83 (dd, 1H, J=1.6 10.6 Hz).

1-(4-bromophenyl)prop-2-en-1-one

RMN $^1$H (CDCl$_3$, 400 MHz): δ 7.71 (d, 2H), 7.52 (d, 2H), 7.01 (dd, 1H, J=10.6 17.1 Hz), 6.33 (dd, 1H, J=1.6 17.1 Hz), 5.86 (dd, 1H, J=1.6 10.6 Hz).

1-(4-methoyphenyl)prop-2-en-1-one

RMN $^1$H (CDCl$_3$, 400 MHz): δ 7.81 (m, 2H), 7.04 (dd, 1H, J=10.5 17 Hz), 6.82 (m, 2H), 6.26 (dd, 1h, J=1.8 17.1 Hz), 5.74 (dd, 1H, J=1.8 10.5 Hz), 3.74 (s, 3H).

1-(p-tolyl)prop-2-en-1-one

RMN $^1$H (CDCl$_3$, 400 MHz): δ 7.74 (d, 2H), 7.17 (d, 2H), 7.05 (dd, 1H, J=10.6 17.3 Hz), 6.3 (dd, 1H, J=1.7, 17.1 Hz), 5.79 (dd, 1H, J=1.7 10.6 Hz), 2.31 (s, 3H).

1-(o-tolyl)prop-2-en-1-one

RMN $^1$H (CDCl$_3$, 400 MHz): δ 7.31 (m, 1H), 7.24 (m, 1H), 7.12 (m, 2H), 6.65 (dd, 1H, J=10.5 17.4 Hz), 6.01 (dd, 1H, J=1.4 17.4 Hz), 5.89 (dd, 1H, J=1.3 10.5 Hz), 2.29 (s, 3H).

2-methylene-1-phenyldodecan-1-one

RMN $^1$H (CDCl$_3$, 400 MHz): δ 7.65-7.62 (m, 2H), 7.45-7.41 (m, 1H), 7.37-7.30 (m, 2H), 5.71 (d, 1H), 5.45 (s, 1H), 2.35 (t, 2H), 1.42-1.34 (qt, 2H), 1.26-1.15 (m, 14H), 0.77 (t, 3H).

11-methylenetricosan-12-one

RMN $^1$H (CDCl$_3$, 400 MHz): δ 5.93 (s, 1H), 5.66 (s, 1H), 2.63 (t, 2H), 2.23 (t, 2H), 1.24 (qt, 34H), 0.86 (t, 6H).

4,4-dimethylpent-1-en-3-one

RMN $^1$H (CDCl$_3$, 400 MHz): Methylene protons. δ 6.5 (dd, 1H, J=10.3 16.9 Hz), 6.03 (dd, 1H, J=2.3 17.0 Hz), 5.33 (dd, 1H, J=2.2 10.4 Hz).

5-methylhex-1-en-3-one

RMN $^1$H (CDCl$_3$, 400 MHz): Methylene protons. δ 6.03 (dd, 1H, J=10.5 17.6 Hz), 5.87 (dd, 1H, J=1.2 17.6 Hz), 5.46 (dd, 1H, J=1.2 10.5 Hz).

Non-1-en-3-one

RMN $^1$H (CDCl$_3$, 400 MHz): Methylene protons. δ 6.25 (dd, 1H, J=10.5 17.7 Hz), 6.11 (dd, 1H, J=1.3 17.7 Hz), 5.72 (dd, 1H, J=1.3 10.5 Hz).

3-methyleneoctan-2-one

RMN $^1$H (CDCl$_3$, 400 MHz): Methylene protons. δ 5.9 (s, 1H), 5.66 (s, 1H).

4-methylenenon-1-en-3-one

RMN $^1$H (CDCl$_3$, 400 MHz): Methylene protons. δ 6.79 (dd, 1H, J=10.5 17.2 Hz), 6.16 (dd, 1H, J=1.8 17.1 Hz), 5.85 (s, 1H), 5.69-5.65 (s+dd, 2H).

Methyl 2-methylene-3-oxobutanoate

RMN $^1$H (CDCl$_3$, 400 MHz): Methylene protons. δ 5.8 (s, 1H), 5.77 (s, 1H).

Methyl 4-oxohex-5-enoate

RMN $^1$H (CDCl$_3$, 400 MHz): Methylene protons. δ 6.18 (dd, 1H, J=10.3 17.7 Hz), 6.09-6.04 (overlapping dd, 1H, J=1.2 Hz), 5.69 (dd, 1H, J=1.3 10.3 Hz).

Methyl 3-methylene-4-oxopentanoate

RMN $^1$H (CDCl$_3$, 400 MHz): Methylene protons. δ 5.99 (s, 1H), 5.78 (t, 1H, J=1.1 Hz).

Methyl 3-methylene-4-oxohex-5-enoate

RMN $^1$H (CDCl$_3$, 400 MHz): Methylene protons. δ 6.74 (dd, 1H, J=10.6 17.1 Hz), 6.13-6.09 (overlapping dd, 1H, J=1.6 Hz), 5.98 (s, 1H), 5.80 (t, 1H, J=1.1 Hz), 5.63 (dd, 1H, J=1.7 10.5 Hz).

The invention claimed is:

1. A process for preparing an α-methylene ketone, the process comprising reacting a ketone with formaldehyde in the presence of a catalyst which is an organic compound comprising at least one acid function or the corresponding salt, ester or amide thereof and at least one amine function or the corresponding ammonium salt, or a zwitterion thereof, wherein the reaction is conducted in the presence of an additional acid and wherein the catalyst is a compound of the general formula (II):

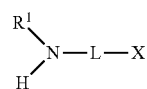

(II)

wherein R$^1$ is H or a hydrocarbon residue which is optionally interrupted by one or more heteroatoms and/or heteroatom(s) containing groups and/or which are optionally substituted with one or more functional groups, X is an acid function or the corresponding salt, ester or amide, and L is a linker, which has 1 to 6 atoms between N and X, wherein any atom of R$^1$ is optionally attached to any atom of L to form a ring, or the corresponding ammonium salt of the amine function;

or a zwitterion thereof.

2. The process according to claim 1, wherein the ketone has the general chemical formula (I)

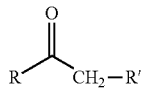 (I)

wherein R is a hydrocarbon radical which may be interrupted by one or more heteroatoms and/or heteroatom(s) containing groups and/or which may be substituted with one or more functional groups, and R' is H or a hydrocarbon radical which may be interrupted by one or more heteroatoms and/or heteroatom(s) containing groups and/or which may be substituted with one or more functional groups, wherein R and R' together with the —C(O)—CH$_2$— moiety may form a ring.

3. The process according to claim 2, wherein in the ketone of formula (I) the R and R' independently of each other comprise 1 to 30 carbon atoms.

4. The process according to claim 2, wherein in the ketone of formula (I) the hydrocarbon radicals independently are alkyl which may be linear or branched, alkenyl which may be linear or branched, alkynyl which may be linear or branched, cycloalkyl, or aryl, or combinations of any of these groups.

5. A process for preparing an α-methylene ketone, the process comprising reacting a ketone with formaldehyde in the presence of a catalyst which is an organic compound comprising at least one acid function or the corresponding salt, ester or amide thereof and at least one amine function or the corresponding ammonium salt, or a zwitterion thereof, and also in the presence of an additional acid, wherein the additional acid is selected from the group consisting of HCl, HBr, HI, H$_2$SO$_4$, HClO$_4$, HNO$_3$, and H$_3$PO$_4$.

6. The process according to claim 1, wherein the catalyst is selected from the group consisting of glycine, valine, serine, methionine, cysteine, proline, sarcosine, β-alanine, phenylalanine, aminomethylphosphonic acid, taurine, methylalanine, isoleucine, and tert-leucine, preferably valine, proline, β-alanine, glycine and methylalanine, more preferably valine, β-alanine, glycine and methylalanine.

7. The process according to claim 1, wherein the reaction is conducted in the presence of a solvent.

8. The process according to claim 1, wherein the catalyst is present at an amount of at least 1 mol %, based on the amount of the ketone.

9. The process according to claim 1, wherein the catalyst is present at an amount of less than 90 mol %, based on the amount of the ketone.

10. The process according to claim 1, wherein the ketone is present at a concentration of less than 5 mol/l.

11. The process according to claim 2, wherein the molar ratio of catalyst to further acid is in the range of 0.1 to 3.0.

12. The process according to claim 1, wherein the formaldehyde is present at an amount of at least 150 mol %, based on the amount of the ketone.

13. The process according to claim 1, wherein the reaction is conducted at a temperature in the range of 25° C. to 200° C.

14. The process according to claim 7, wherein the reaction is conducted in the presence of an organic solvent selected from the group consisting of DMSO, THF, methyl-THF, ethylacetate, toluene, benzene, acetone, dimethyl formamide, acetonitrile, alcohols, halogenated solvents, and ketones with the exception of ketones bearing a —CH$_2$— moiety next to the carbonyl group.

15. The process according to claim 9, wherein the catalyst is present at an amount of less than 60 mol %, based on the amount of the ketone.

16. The process according to claim 15, wherein the catalyst is present at an amount of less than 45 mol %, based on the amount of the ketone.

17. The process according to claim 16, wherein the catalyst is present at an amount of less than 25 mol %, based on the amount of the ketone.

* * * * *